United States Patent [19]

Iversen et al.

[11] 4,229,656
[45] Oct. 21, 1980

[54] X-RAY ORIENTING APPARATUS

[75] Inventors: Arthur Iversen; John Magyar, both of New York, N.Y.

[73] Assignee: Pfizer Inc., New York, N.Y.

[21] Appl. No.: 956,327

[22] Filed: Oct. 31, 1978

[51] Int. Cl.$^2$ .................... G01N 21/00; G21K 5/10; H01J 35/16

[52] U.S. Cl. .................. 250/447; 250/491; 250/523

[58] Field of Search ............. 250/439 P, 439 R, 447, 250/448, 451, 521, 523, 491

[56] References Cited

U.S. PATENT DOCUMENTS

| | | | |
|---|---|---|---|
| 1,877,690 | 9/1932 | Russell | 250/523 |
| 2,264,410 | 12/1941 | Schier | |
| 2,532,967 | 12/1950 | Thompson | |
| 3,045,118 | 7/1962 | Hollman et al. | 250/447 |
| 4,088,893 | 5/1978 | Schroeder | |
| 4,132,900 | 1/1979 | Smith et al. | 250/491 |

OTHER PUBLICATIONS

Radberg, C. and Welander, U., *Maxillo-Facial Radiography with ORBIX*, Siemens-Elema AB, Stockholm, Title, Contents, Position, Introduction, and Technical Description pages.

*Primary Examiner*—Alfred E. Smith
*Assistant Examiner*—T. N. Grigsby
*Attorney, Agent, or Firm*—Connolly and Hutz

[57] ABSTRACT

Precise orientation of an x-ray apparatus in which the x-ray tube and film cassette are mounted on opposite ends of a C-shaped arm is facilitated by a chair for the patient which is precisely movable along X and Y axes with the digital readout of adjusted positions. The angular rotation of the chair on its vertical support also has a digital readout. All of the readouts may be adjusted to zero at basic positions to facilitate adjustment. The angle of the C-arm is displayed by an inclinometer which also may be adjusted to zero at a basic position. The chair has an adjustable cradle for the head and the entire chair may be tilted to an acute angle to support unconscious or disabled patients without interfering supports. Orientation of the C-arm is also facilitated by a light source removably mounted over the film cassette, which designates the exit point of the x-ray on the patient.

10 Claims, 7 Drawing Figures

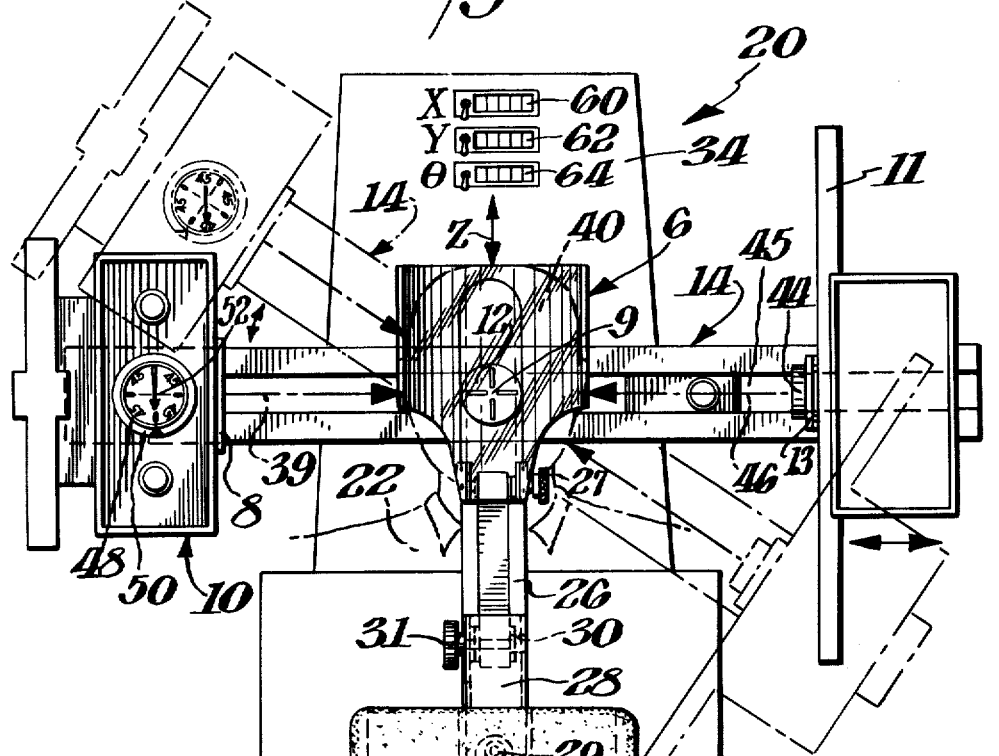
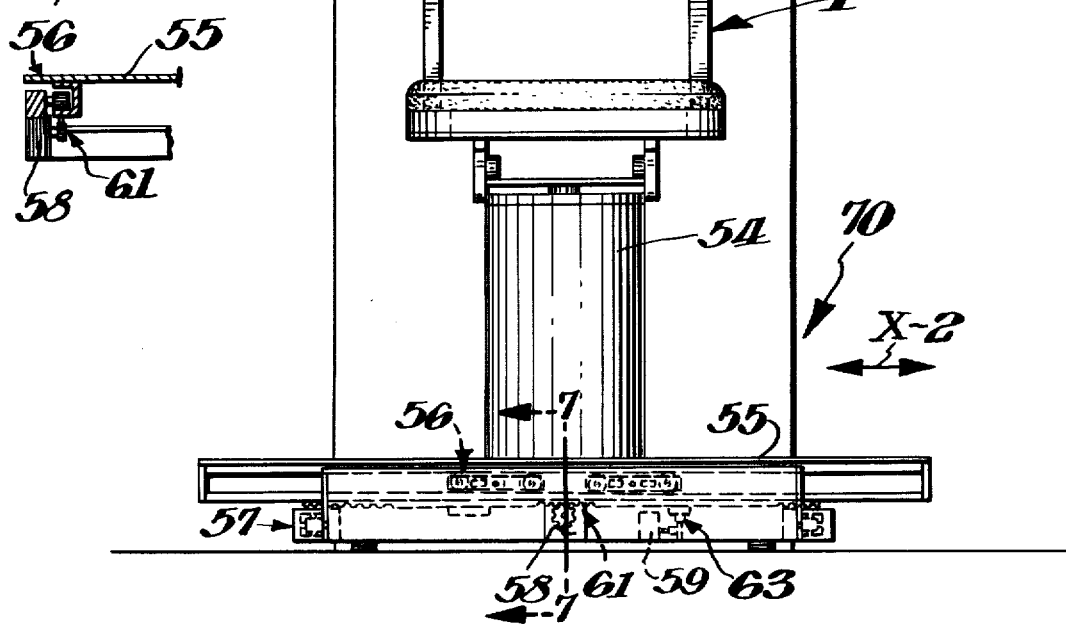

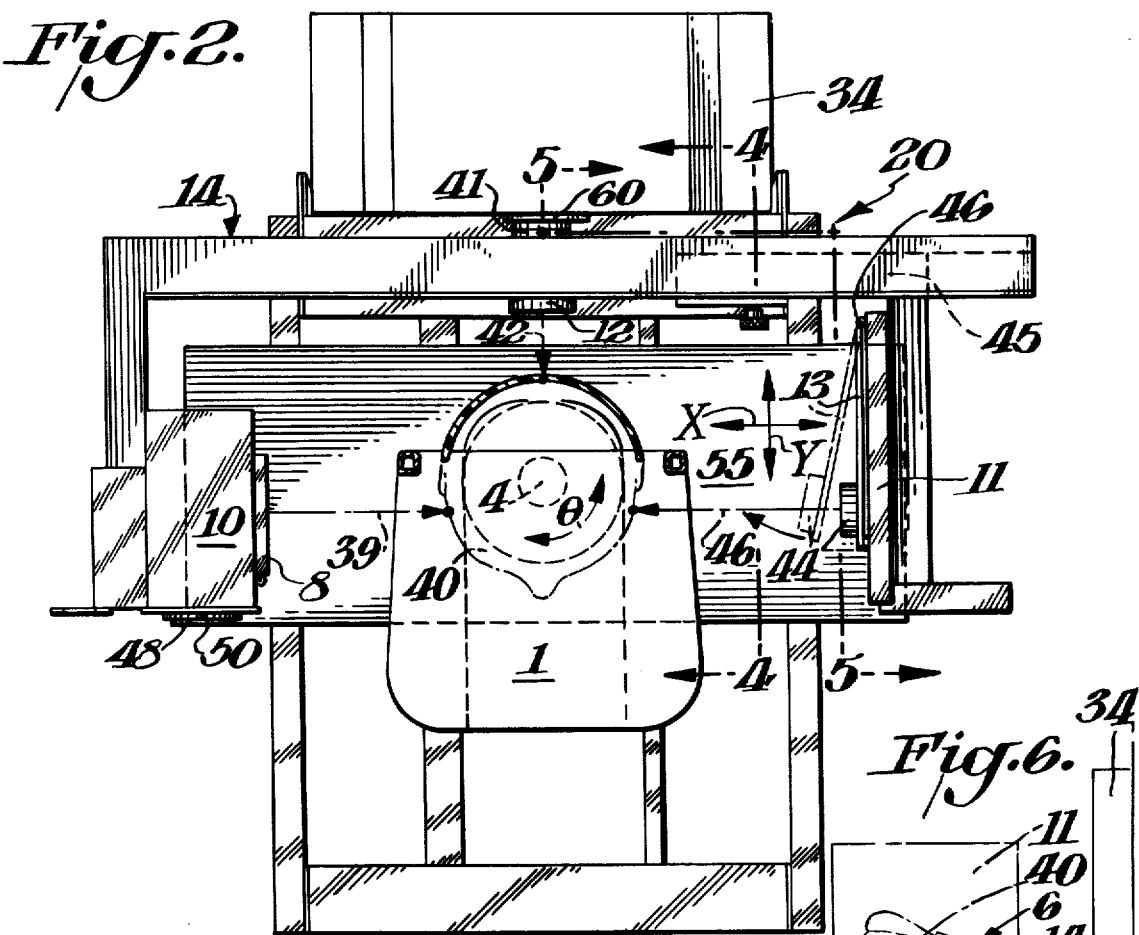
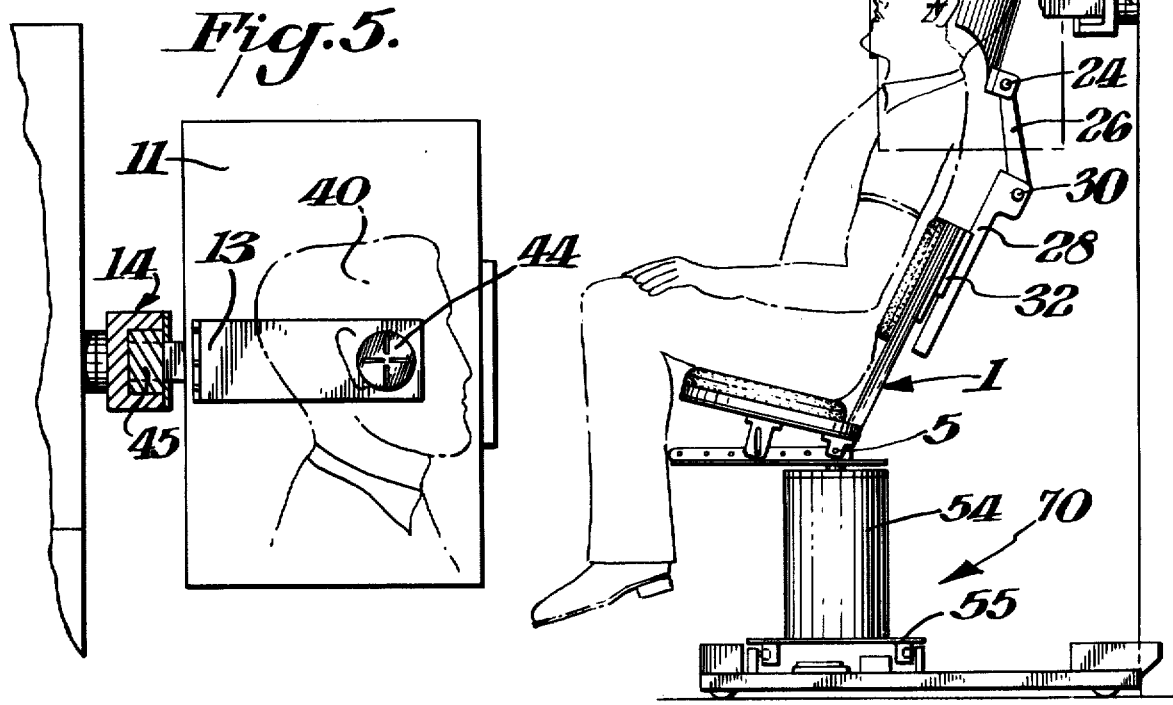

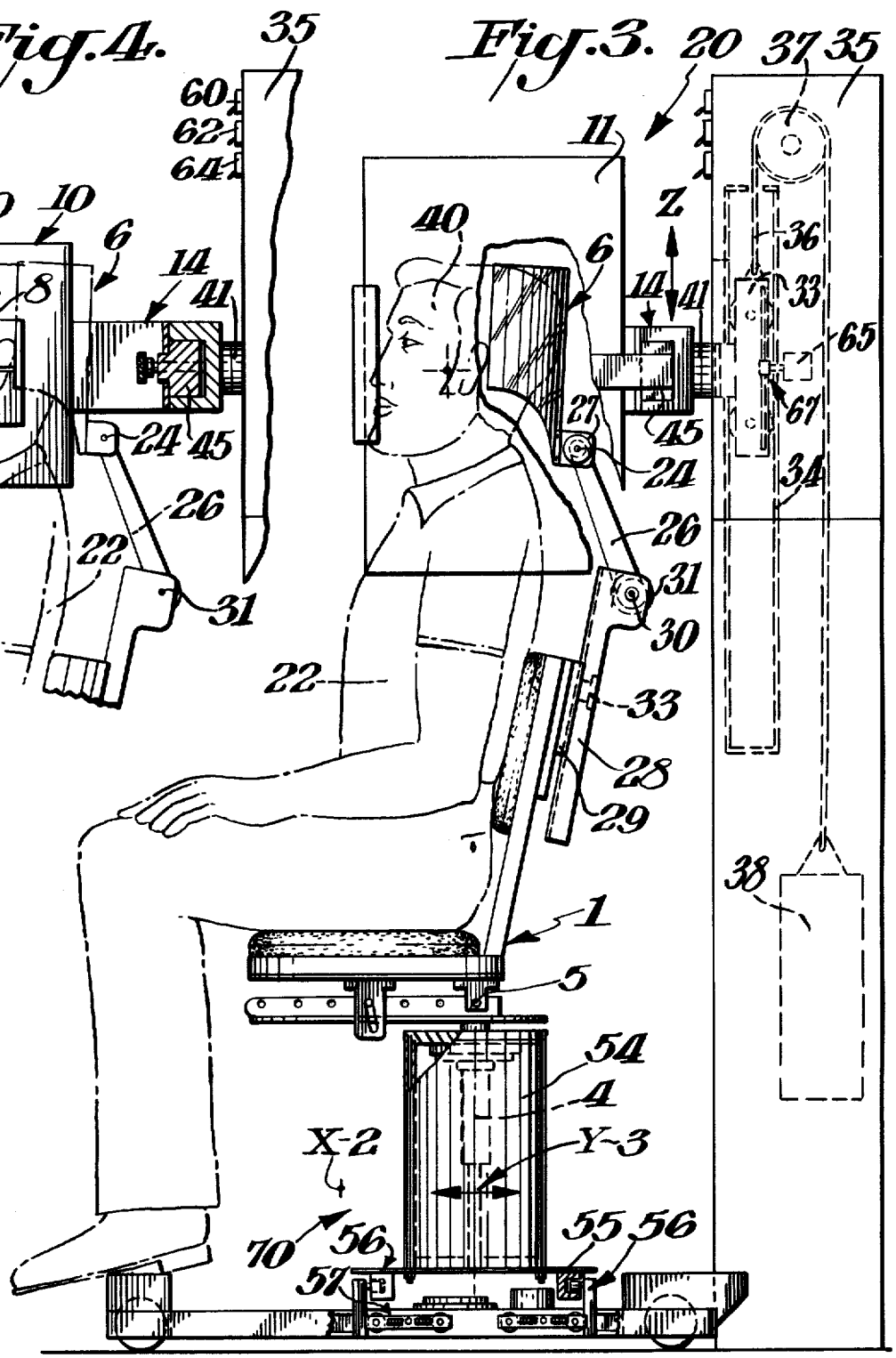

X-RAY ORIENTING APPARATUS

BACKGROUND OF THE INVENTION

Radiology of the head, face and neck is generally done with conventional x-ray equipment in smaller hospitals, however, in larger institutions where more sophisticated techniques and diagnosis are carried out, dedicated equipment is utilized to enable a more precise and repeatable technique to be achieved for the various examinations. Radiographic diagnosis of the head, face and neck presents some unusual problems because of the complexity of the skull and the heavy over layers of bony material that must be penetrated in order to visualize internal parts. In order to achieve proper visualization of certain parts, precise positioning and angulation of the skull with respect to the x-ray machine must be achieved. This is necessary in order to provide the proper view as well as to avoid obstructing irregular bone masses which would obilterate the part to be viewed.

The difficulties encountered in Radiography of the head, face and neck is indicated by the fact that there are six major procedures which are frequently done by tomographic technique because conventional technique frequently does not provide adequately diagnostic information. These techniques are: (1) Inner Ear, (2) Facial Bone, i.e. Orbits, Sinus, (3) Sella Turcica, (4) Odontoid process, (5) entire Cervical Spine, (6) TM Joint. Moreover, the fact that there are a large number of medical sub specialties, each attending to various aspects of the head, face and neck is further indication of the complexity of this region.

In an effort to simplify head, face and neck procedures and to provide maximum precision and repeatabilty, dedicated systems have been designed and marketed. The oldest system is the Franklin Head Unit which has been around for over 30 years and the other system, which is fairly recent, is the Siemens Orbix. The Franklin Head Stand which is utilized extensively because of its' relatively moderate price utilizes an x-ray tube and collimator mounted on a C-arm structure which is then attached to a vertical column. The C-arm structure can travel vertically as well as rotate. To perform a given technique the patient is placed in a roll-around chair, the patient is then rolled into position inside the arm structure, that is, between the x-ray tube, collimator and film tray. He then has his head clamped with the head clamp. The light from the collimator then shines down upon that part of the head to be radiographed after the appropriate angle is indicated on the rotational part of the C-arm. The collimator is then opened to the appropriate aperture. The x-ray is then taken.

This type of positioning has a number of limitations with respect to precision. In addition, the machine is not capable of high resolution magnification work. One of the main difficulties with the machine is that by only being able to utilize the entering ray as simulated by the collimator light a precise angling of the patients head is difficult to determine, that is, there could be a slight rotational effect on the head and this could not be determined with any degree of precision because there is only one degree of freedom with the light. The use of the single light does not permit the use of land marks along the side of the head, such as the line of the inner ear, etc. In addition, the presence of the head clamp which serves to center the head, makes difficult side angle shots of the head and therefore limits the use of the system for many lateral exposures.

To introduce high precision and repeatability as well as enabling more versatility, the Orbix was designed by Siemens. This unit require a dedicated room and is quite expensive, however, it offers great precision in alignment. It is a ceiling mounted unit with precision in all motions. The C-arm unit which is mounted to the main arm can move vertically as well as rotate and the film tray can also move independently. It has two precise location lights which provide orthoginal alignment, one in the collimator and one at the pivot point at right angles to the collimator. The two alignment lights provide cross-hair lighted lines for precise positioning which enables precision motion to be prescribed from any one location to another location. To utilize the Orbix requires a fair amount of calculation work. The Operations Manual provides a series of steps to obtain a precise position. A cursory examination of the Orbix manual illustrates the above.

The precision of the Orbix system is limited by the ability of the operating technician to provide precise initial marks, whether it be a TM joint or otherwise. Typically one might expect precision here of plus and minus several millimeters. The precision of the machine thereafter probably can be measured in fractions of a millimeter, therefore the overall preciseness is operator determined.

It is an object of the present invention to enable precise positioning of the various procedures of the head, face and neck to be achieved.

It is yet another object of the present invention to permit this precise positioning to be done in a simple, repeatable and straight forward fashion.

It is still yet another object of the present invention to enable radiographs to be obtained from any arbitrary angle on the patient by use of a unique radio-transparent head positioning and immobilization device.

It is a further object of the present invention to permit an additional degree of freedom in visualizing the x-ray path than has been heretofore available.

It is yet another object of the present invention to provide a small compact system that may be stored in a corner of a room without requiring large amounts of space.

SUMMARY

The above objectives are achieved by the design of a special chair and head immobilizing device. The chair is constructed so as to move in the X-axis, Y-axis and may rotate about its' central axis. The chair can be further tilted back in an approximate ten to fifteen degree angle so as to make use of gravity for immobilizing the patient without the need for straps or other undesirable restraints. It has been determined that the minimum angle desirable is approximately 10°, but, depending upon patient condition, i.e. cooperative or uncooperative the angle may be increased as necessary. The head restrainst is molded from approximately ⅛" thick or less polycarbonate, such as Lexan. The shape is molded precisely to conform to the general shape of the head. The head immobilizer may be tilted back and forth at some small angle in order to accommodate the natural position of various patients. In the normal starting position, the axis of rotation of the chair intersects approximately the central ray of the x-ray beam, i.e. positioned in such a way between the x-ray tube and film tray of the C-arm structure. The C-arm structure also may be either fixed to the wall or vertically adjusted and rotated in a vertical plane. On the C-arm structure are mounted an x-ray tube and collimator and at the end opposite a film tray. The x-ray tube head contains a suitable light source and collimator with cross-hairs. It also has mounted on its surface an inclinometer to precisely indicate the angle of inclination of the C-arm. On the C-arm proper another cross-hair light is positioned which may be slid along the C-arm in a parallel direction, i.e. parallel to the central ray, to the left or right as shown to adjust for desired magnification. In addition, there is a further light source which is on a swinging arm so that it may pivot to the center of the film tray and project also a cross-hair light. When not required, it pivots out of the way so as not to obstruct any portion of the film mounted on the film tray.

BRIEF DESCRIPTION OF THE DRAWINGS

Novel features and advantages of the present invention will become apparent to one skilled in the art from a reading of the following description in conjunction with the accompanying drawings wherein similar reference characters refer to similar parts and in which:

FIG. 1 is a front elevational view of one embodiment of this invention with a portion of a patient shown in phantom outline and an inclined position of the C-shaped arm also shown in phantom outline;

FIG. 2 is a top plan view of the embodiment shown in FIG. 1;

FIG. 3 is a left side elevational view of the embodiment shown in FIGS. 1 and 2;

FIG. 4 is a cross-sectional view taken through FIG. 2 along the line 4—4;

FIG. 5 is a cross sectional view taken through FIG. 2 along the line 5—5;

FIG. 6 is a left side elevational view similar to FIG. 3, but with the chair and patient tilted backwardly; and FIG. 7 is a cross sectional view taken through FIG. 1 along the line 7—7.

DESCRIPTION OF THE PREFERRED EMBODIMENT

In FIGS. 1-3 is shown an apparatus 20 for supporting and orientating x-ray units including a chair 1, which is movable along X axis 2 and Y axis 3 and which also may rotate about its vertical central axis 4. Chair 1 may also have its seat tilted backwardly about intermediate horizontal axis 5 as shown in FIG. 6 at an angle of approximately 10° to cradle an unconscious or disabled patient 22 without requiring any supports which may obstruct or interfere with the x-rays. Support of patient 22 is facilitated by cradling headrest 6, which is, for example, molded into an arcuate shape from a sheet of clear plastic such as ⅛" thick polycarbonate, of low x-ray absorption characteristics, such as Lexan made by General Electric Company. The cross sectional shape is substantially circular and just sufficient to conform to the back of the head leaving the area of the ears and forward thereof clear for the passage of x-rays. There are no abrupt geometry changes in the headrest, because of the smooth gradual curve, thereby film artifacts are held to a minimum. Head restraint or cradle 6 may be tilted back to various positions on pivot 24 mounted on top of arm 26 and retained in the selected position by lock knob 27. Arm 26 is rotatably connected to U-shaped slide 28 by pivot 30 and retained in the selected position by lock knob 31. U-shaped slide 28 may be vertically adjusted to various vertical positions relative to chair 1 by raising or lowering slide in guide track 32, and retained at the selected position by tightening locking knob 29.

C-arm structure 14 is rotatably mounted by a bearing structure 41 to a carriage 33. The carriage 33 is vertically movable along a Z axis within a guide track 34. The C-arm/carriage assembly is centrally balanced by use of a cable 36 over a pulley 37 to a counterweight 38. Once the C-arm is properly positioned on the Z axis, the cable 36 is locked by an electro-magnetic clutch built onto pulley 37. C-arm 14 is rotated about pivot axis 9 through the support bearing 41 to provide various angles of inclination and is locked against rotation when properly positioned by an electro-magnetic clutch. X-ray tube and collimator 10 are mounted on one end of C-arm 14 and film cassette 11 is mounted on the other end of C-arm 14. A light source 8 with suitable cross hairs is mounted on the x-ray tube and collimator 10 to provide a ray of light 39 which designates the central ray of the x-rays impinging on the patient's head 40 shown in FIGS. 1 and 2. Light source 12 is disposed on the pivot axis 9 of C-arm 14 and designates another reference point on the head 40 of a patient by beam 42. Additional light source 44 emits beam 46 which designates the central ray of the x-rays exiting from head 40 of the patient. Source 44 is mounted on arm 13, which is movable about pivot 46 out of the path of the x-rays after positioning is accomplished.

FIG. 1 also shows inclinometer 48 mounted on x-ray unit 10 which designates the angle of inclination of C-arm 14. Inclinometer 48 has an adjustable bezel 50 which permits the indicia 52 to be set to zero at basic inclinations to facilitate the setting to sequential positions.

Chair supporting pedestal 54 is mounted to a carriage platform 55 to allow movement of the chair and pedestal in the X and Y direction by roller and guide assemblies 56 and 57 respectively. Potentiometers 58 and 59 sense the X-Y positions by a rack and pinion system 61 and 63 as shown in FIG. 7. The chair rotational angular position is also sensed by a potentiometer using gear coupling. The X, Y and Z coordinates are indicated on displays 60, 62 and 64 readily visible to the technician. Arm 14 in the phantom position shown in FIG. 1 is disposed at an inclined position about pivot axis 9 for which inclinometer 48 has been set to zero by movable bezel 50.

Position indications are then read out from the various position indicators. The position indicators provide a read-out for the X, Y and horizontal rotation of the chair. These positions are digitally read-out to simplify operation and all indicators may then be zero set, i.e. adjusted so that all readings indicate zero in this position, i.e. when all landmarks or cross-hairs are lined up. The technician is able to adjust the chair in X, Y and horizontal rotation planes and the C-shaped arm in the vertical or Z plane to the proper relative positions for taking an x-ray for the examination desired. This eliminates confusion that may arise if the operator had to add or substract the appropriate movements to any sequential position from the reference position. In addition this also provides ease and simplicity of operation to return to the reference position if there are any problems, i.e. improper picture to determine if the reference position was proper. The read-out is set to zero. The ability to add the X or Y correction reference is by providing each read-out with the capacity to permit entry into the circuits by another potentiometer, which may than provide bucking voltage to cancel out the indicated reading. Any movement thereafter from the reference position to the position for the examination is indicated in an absolute fashion. The technology provides an automatic "memory" feature. The adjustment of the zero potentiometer automatically is fixed until the next patient. The desirability of this approach is several fold.

It eliminates the time and record keeping required by the addition and subtraction necessary in going from the readings as indicated in the reference position to the examination position. It avoids potential for error in arithmatic, misplacement during the examination. It provides the convenience of having the direct reference position change required from reference to examination in a direct manner. X, Y and horizontal rotation of the chair is sensed by 0.1% linear potentiometers (10 turns) having a gear/rack mechanical relation.

Operation of the chair is as follows:

The chair 1 is slid forward in the Y axis 3 so as to enable seating of the patient in an unobstructed fashion. After the patient has been seated, the head restraint 5 is then adjusted by adjustment at 24 and 30 for a comfortable angle. In this fashion patients who are uncooperative or in trauma are in a very comfortable position and are made cooperative in the best possible fashion. This is in contrast to the supine position which is typically on a hard top table which is generally quite uncomfortable. When a patient is injured or frightened, this can present more problems. Once the patient is positioned, a typical technique would be to swing the C-arm 14 in the horizontal position. The patient would then be rotated so as to look directly into the collimator if one were doing an AP study. The sliding cross-hair light 12 is then adjusted for the desired magnification. The patient chair is then moved on the X axis 2 so that the cross-hair light precisely defines the landmark on the patient's head, such as the TM joint, ear or other appropriate place. The machine is then angled so as to accommodate the angle of the tilt of the chair, that is 10 to 15 degrees about horizontal axis 5 as well as any anatomical variations. This is usually done using landmarks on the patient. The inclinometer 12 which is in a rotating bezel is now adjusted to zero, by rotation of the bezel ring to zero, this then provides an arbitrary zero set. This is a critical and important feature of the system of this invention. It not only permits adjustments to be made for any changes in the chair angle or head angle, but also and perhaps most important, enables zero set adjustments to take care of variations in skeletal structure from patient to patient. This permits a more accurate zero set, an advantage that the ceiling mounted units do not have and which is not even feasible in the older floor stand models.

With the angle now set for zero, for a prescribed view such as Townes, the C-arm is now angled the appropriate number of degrees. The film tray indicator light 13 which has been swung over the film tray and over the film, now acts as a pointer towards the exiting central ray from the x-ray tube collimator 10. This is a very important feature inasmuch that it enables the technician to make corrections for anatomical differences from patient to patient for such any given view. None of the known systems have any means for correction. When the positioning is complete, the patient is now ready for the x-ray. The film tray light pointer 13 is now swung out of the way and an x-ray is taken. In clinical use to date, the present system has shown itself to be simple and easy to use. What has turned out to be a very useful feature is the film tray light pointer 13. For many of the less precise examinations the technicians have utilized the cross-hairs of the collimator 11 for the entering central ray and then simply adjusted the patients position. The present system utilizes the light pointer on the film tray 13 so as to achieve the desired angle. The result of this appears to be a lesser need for the precise X-Y and rotational coordinate positioning capability. They visualize from land marks on the skeletal anatomy for both entering central ray 39 and exiting ray 46. This raises the possibility that a chair may be constructed utilizing an air cushion effect, that is a blower will lift the chair a fraction of an inch off the ground and the technician then has perfect X-Y and rotational motion available to him with great ease, however, there are no precise coordinates available using this technique and it remains to be determined as to whether this is a suitable technique.

There is a further difference between the present chair and C-arm combination in this invention and other dedicated head units. In other known units the patient is stationary and the x-ray tube and film tray move with respect to the patient. This system, however, provides three degrees of freedom in the chair, X-Y and rotate and two degrees of freedom in the C-arm system. The earlier floor stand units utilize a simple chair on wheels in which a patient is positioned, rolled over to the head clamp, is clamped into place and is thereafter immobile. The result of this is that not only is precision difficult or impossible to achieve but in addition, it is awkward to achieve convenient positioning for some views. Repeating views on subsequent visits is also difficult.

Later ceiling mounted units the other hand, in order to achieve all the degrees necessary to do all the examinations utilize a large number of complex motions in a single system, starting out with a ceiling mount rotary motion in the horizontal plane. The C-arm itself is capable of vertical motion, rotational motion and the tray has additional motions. The result of incorporating all degrees of freedom into a single system is a very expensive unit, in addition to being large and bulky and therefore requiring a dedicated room for its's use. A further complication of known units is in the way patient immobilization is achieved—use of a head clamp or of belts and straps. If the patent is injured or in a delicate condition, the straps and clamps may not prove to be a desirable aspect, especially those patients who have suffered severe trauma. This system on the other hand does not require belts or straps. The approximate ten to fifteen degree inclination of the chair and contoured radiotransparent head support utilize the pressure of gravity, the comfort of a slightly reclined chair to immobilize the patient, proven to be most effective.

This system by providing the universal C-arm capability, that is a C-arm which can rise and lower in the vertical plane, as well as rotate in the vertical plane is a stand alone system on its own. The additional degrees of required freedom are then provided by the chair, that is, X-Y and rotate in the horizontal plane. In this manner the same precision may be achieved with the present system mechanically, as is achieved with the Siemens system. An unexpected benefit of this combination of chair and stand is that a very compact and relatively inexpensive system results. In addition, it permits maximum versatility of the system. When one wishes to do extremeties or other parts of the body, the chair, which is on wheels and has been locked with respect to the x-ray machine in a fixed, pre-aligned position is now released and moved into a corner. A float top table on wheels is rolled over and conventional radiography may then be practiced. The economic advantage of this type of system is significant in that a system with substantially lower cost can be the result as compared to the expensive approach of the ceiling mounted system. Chair assembly 1 could be replaced by a table top (not shown) mounted to pedestal 54 for x-raying patients in a horizontal position.

We claim:

1. An x-ray orienting apparatus having an x-ray source and film cassette mounted on opposite ends of a C-shaped arm which has a central pivot axis vertically movable on a support post comprising a patient-supporting chair, movable means mounting the chair on a horizontal floor whereby the chair may be precisely oriented on the floor relative to the x-ray beam, and display means coordinated with movement of the chair on the floor whereby adjusted positions are precisely indicated.

2. An x-ray orienting apparatus as set forth in claim 1, wherein the chair is mounted on guide means having freedom of motion in two directions and to rotate.

3. An x-ray orienting apparatus as set forth in claim 2, wherein potentiometer means is connected to the guide means, and the display means is connected to the potentiometer means.

4. An x-ray orienting apparatus as set forth in claim 1, wherein the chair has a seat, tilting means connecting the seat to the chair whereby the seat may be inclined to various acute angles for cradling a patient.

5. An x-ray orienting apparatus having an x-ray source and film cassette mounted on opposite ends of a C-shaped arm which has a central pivot axis vertically movable on a support post comprising a patient-supporting chair, an arcuate head support being adjustably connected to the chair, the head support being constructed and arranged to cradle the back of an average-sized head to leave the frontal area of the head unobstructed for passage of x-rays.

6. An x-ray orienting apparatus as set forth in claim 5, wherein the arcuate head support has smooth contours without any abrupt changes whereby relative distoration of x-rays passing through the head support is avoided.

7. An x-ray orienting apparatus as set forth in claim 6, wherein the arcuate head support has a substantially circular contour.

8. An x-ray orienting apparatus having an x-ray source and film cassette mounted on opposite ends of a C-shaped arm which has a central pivot axis vertically movable on a support post comprising a light projecting means for designating the exit point of the x-ray, movable means mounting the light projecting means optionally over the film cassette and remote from it whereby the light source designates the exit point of the central x-ray during positioning and is swung out of the path of x-ray while an exposure is being made.

9. An x-ray orienting apparatus as set forth in claim 8, wherein the movable means comprises a swinging arm.

10. An x-ray orienting apparatus having an x-ray source and film cassette mounted on opposite ends of a C-shaped arm which has a central pivot axis vertically movable on a support post comprising an inclinometer mounted on the C-shaped arm, and movable indicia on the inclinometer whereby it may be set to the zero position when the C-arm is adjusted to a basic setting from which sequential positions are adjusted.

* * * * *